United States Patent [19]

Anspach, III

[11] Patent Number: 5,112,338
[45] Date of Patent: May 12, 1992

[54] SURGICAL INSTRUMENT FOR REMOVING ARTIFICIAL ACETABULAR CUPS

[76] Inventor: William E. Anspach, III, 1349 S. Killian Dr., Lake Park, Fla. 33403

[21] Appl. No.: 653,151

[22] Filed: Feb. 11, 1991

[51] Int. Cl.[5] .............................................. A61B 17/56
[52] U.S. Cl. ........................................ 606/99; 606/81; 606/91; 606/104; 623/22; 173/10
[58] Field of Search ...................... 606/81, 91, 99, 100, 606/104, 172, 180, 80, 86; 623/22; 173/10, 166, 163

[56] References Cited

U.S. PATENT DOCUMENTS

| | | | |
|---|---|---|---|
| 4,111,208 | 9/1978 | Leuenberger | 606/80 |
| 4,124,026 | 11/1978 | Berner et al. | 606/104 |
| 4,271,849 | 6/1981 | Rehder | 606/81 |
| 4,355,931 | 10/1982 | Leuenberger | 606/168 X |
| 4,399,813 | 8/1983 | Barber | 606/180 X |
| 4,662,891 | 5/1987 | Noiles | 606/80 X |

FOREIGN PATENT DOCUMENTS

| | | | |
|---|---|---|---|
| 0026022 | 4/1981 | European Pat. Off. | 606/80 |
| 0327509 | 8/1989 | European Pat. Off. | 623/22 |
| 8802246 | 4/1988 | World Int. Prop. O. | 606/100 |

*Primary Examiner*—Randall L. Green
*Assistant Examiner*—D. Willse
*Attorney, Agent, or Firm*—Jack N. McCarthy

[57] ABSTRACT

A hand-held surgical rotary impact tool and instrument extension for removing artificial hip, or acetabular, cups of a hip joint by rotating the cup a predetermined number of degrees. This rotational limitation is provided by a pin and arcuate groove connection between a fixed housing and rotatable shaft. While instrument extensions are sized to allow for different acetabular, or hip, cups, the cup engaging end can have radially adjustable pins for permitting a variable diameter for connection to a cup.

12 Claims, 3 Drawing Sheets

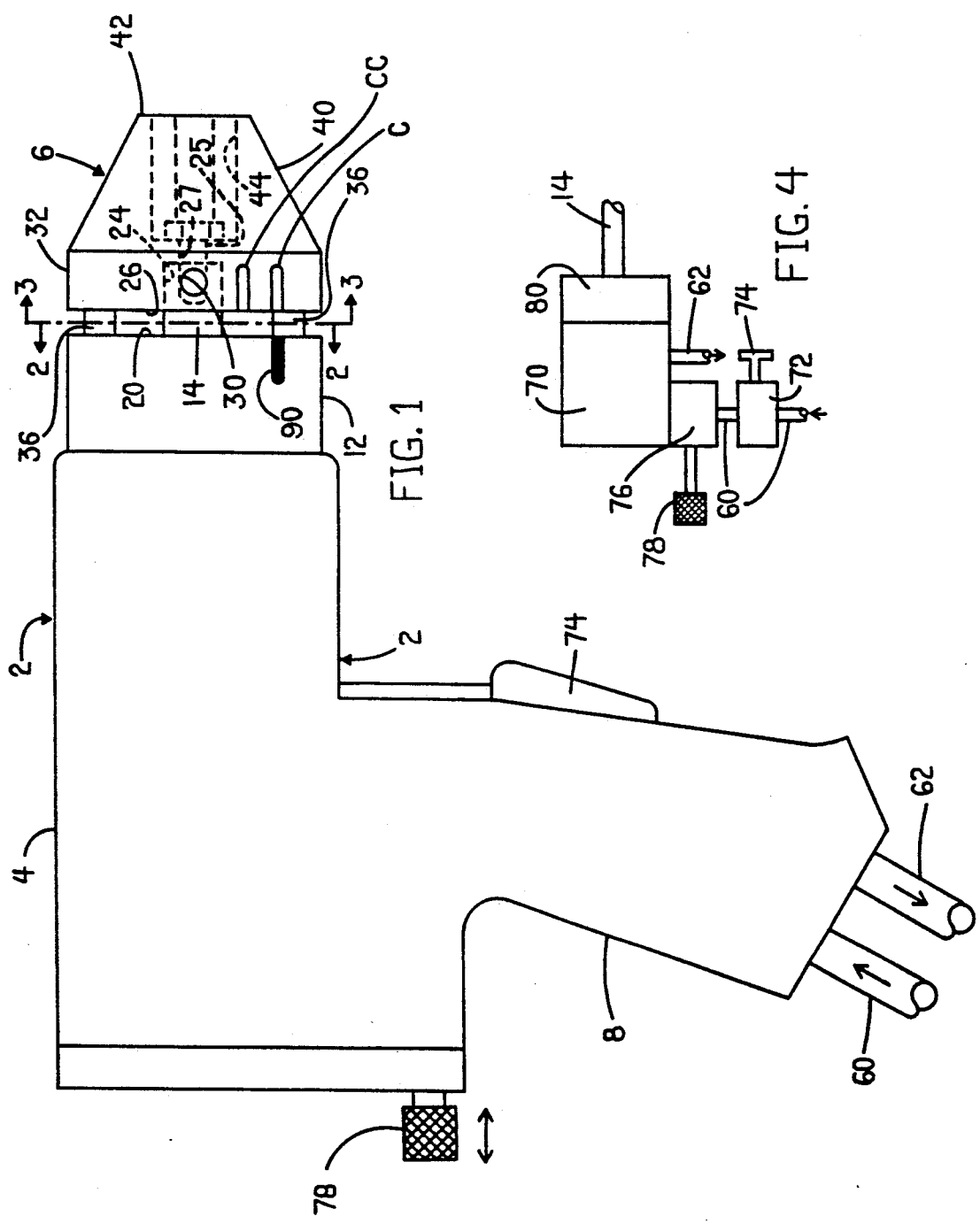

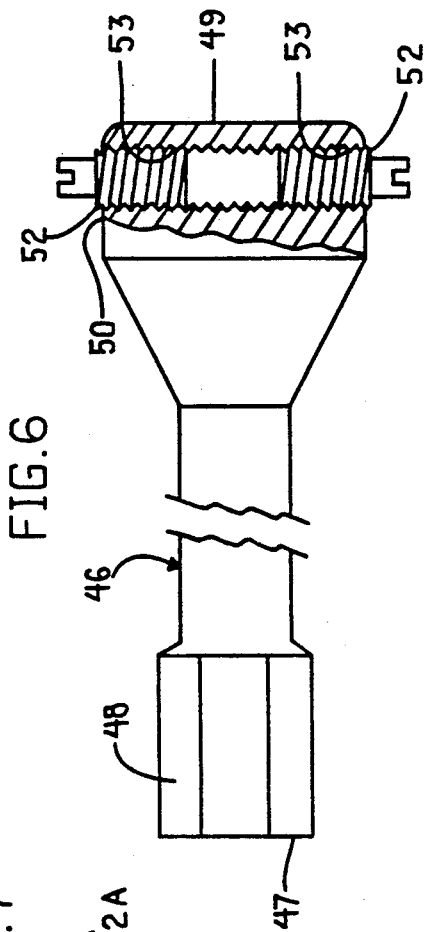
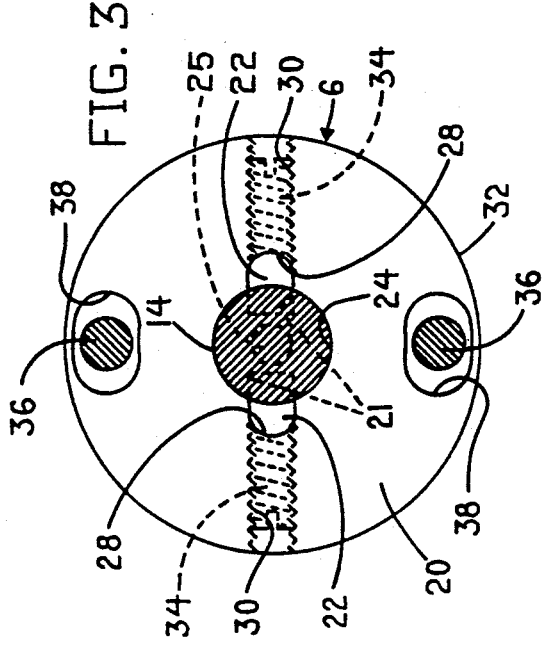
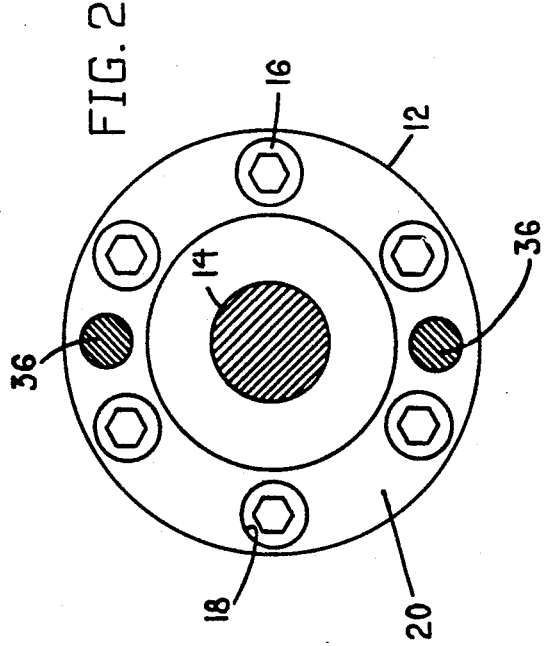
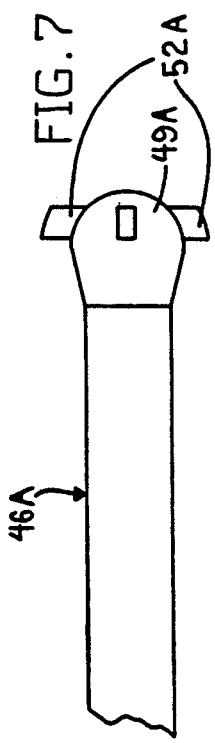

SURGICAL INSTRUMENT FOR REMOVING ARTIFICIAL ACETABULAR CUPS

TECHNICAL FIELD

The invention relates to an apparatus for removing metal and plastic artificial hip implants, specifically the acetabular, or cup side, of the hip.

BACKGROUND OF THE INVENTION

The hip is a ball and socket joint which in its normal state glides freely. Various disease processes commonly attack the surfaces of this joint, causing those surfaces to become rough, thereby increasing the friction load and causing pain as well as limited motion. A common practice is to replace severely diseased hip joints with artificial means. The socket portion is replaced with an artificial acetabular cup. The normal human acetabulum, or hip socket, is quite thin, being approximately ⅛ inch in thickness at the base of the socket, but quite substantial around the peripheral margins. When either a plastic or metal backed cup is placed in the acetabulum, it is first necessary for the surgeon to ream the socket to fit the artificial implant. This requires removing bone from an area where there was very little to start with as concerns the central portion of the socket. If an artificial hip socket has to be removed because of malposition, wear or infection, the only available methods at the present time are to either pry out the implant with various forms of chisels or cut the implant into small pieces and again pry them away from the thin pelvic wall. This surgery is performed deep in the hip joint with limited exposure to surgical instruments, and the operation is frequently bloody; therefore, limiting the surgeon's vision.

Patents related to the subject matter are: U.S. Pat. Nos. 3,752,161; 4,124,026; 4,271,849; 4,355,931; and Russian Patent No. 829,109. The basic standard rotary impact wrench used to remove wheel lug bolts on cars contains a rotary impact mechanism used in subject surgical rotary impact tool to provide repeated rotary impact motion. These wrenches are used throughout the country and are manufactured and sold by numerous companies, some of which are Chicago Pneumatic Co.; Ingersoll Rand Corp.; Florida Pneumatic Co.; and NAPA.

DISCLOSURE OF INVENTION

The object of the present invention is to create an apparatus which will loosen an artificial hip socket by rotary impact. The distance covered by a rotating object varies with the diameter of the object. The central portion of the human hip socket is its thinnest and most fragile area, whereas the periphery of the socket is quite substantial. Thus, if one could loosen an artificial hip socket by rotating it only a few degrees, the central portion would be subject to much less stress than the periphery given a specific amount of rotation. Since the forces required to loosen an artificial socket are considerable, an impact device was employed which would create sufficient torque over a very short time period. The degree of rotation of the impact device must be limited to only a small number of degrees, as one would not desire to spin an artificial hip socket that had protruding extensions on its undersurface as bone damage would occur.

This apparatus consists of a drivable tool extension shaft on whose free end section there is arranged varying sized circular portions with two, or more, protruding pins. These pins fit into the artificial hip socket inside recesses cut into either the plastic or metal cup. The circular portions for metal cups are provided with radially adjustable pins. Rotational fixation is thus accomplished between the artificial cup and the tool extension shaft. Artificial hip cups vary in dimension, necessitating the presence of varying sized circular portions. The tool extension is driven by a standard rotary impact tool similar to those used to remove wheel lug bolts on cars, but with one main significant difference. Since we cannot rotate the artificial hip cup 360° because of the potential for bone damage, the rotation is limited to a few degrees. This is accomplished mechanically by placing fixed axially extending pins in a special circular end plate which is made an immovable portion of the nose of the surgical rotary impact tool through which a modified shaft passes. These pins fit inside arcuate sockets of a predetermined length in a rotational end portion fixed to the end of the modified shaft of the surgical rotary impact tool, limiting its rotation. A tool extension is coupled to the rotational end portion of the impact tool by a hexagonal socket. The tool extension can be rotated in either a clockwise or counterclockwise direction.

BRIEF DESCRIPTION OF THE DRAWINGS

FIG. 1 is a side elevational view of a surgical rotary impact tool;

FIG. 2 is a view taken on the line 2—2 of FIG. 1;

FIG. 3 is a view taken on the line 3-3 of FIG. 1;

FIG. 4 is a diagrammatic view explaining the parts and operation of the rotary impact tool;

FIG. 6 is a view of a tool extension having an end for attachment to the surgical rotary impact tool and an end for insertion into a metal artificial acetabular cup to direct a rotational impact to the outer edge thereof; and FIG. 7 is a fragmentary view showing a modification of the end of a tool extension with a spherical shape which engages a plastic artificial acetabular cup.

BEST MODE FOR CARRYING OUT THE INVENTION

Figure 5:
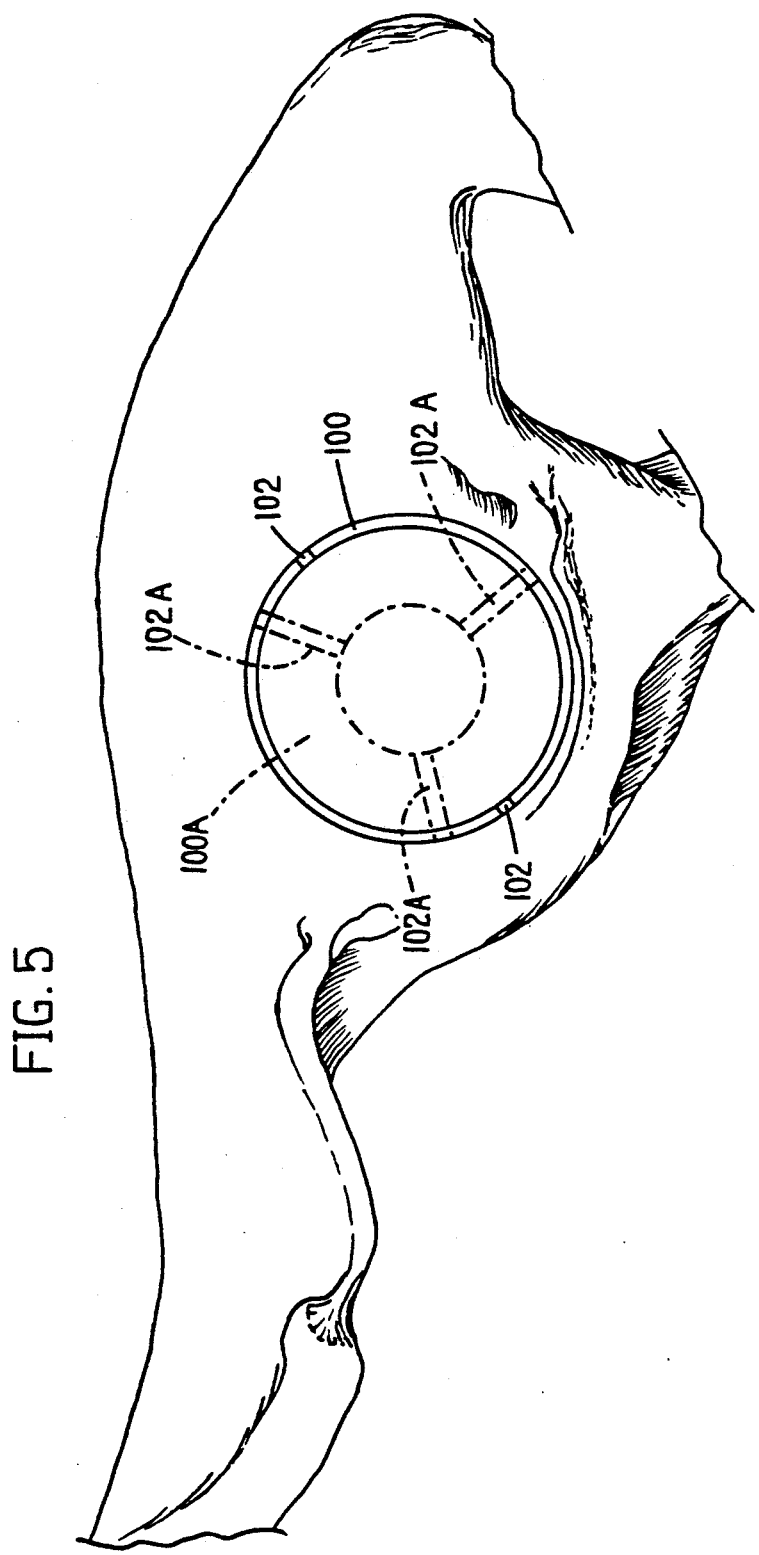
FIG. 5 is a view of an exposed hip with an artificial acetabular cup in place, prepared to be removed by having radial notches cut in the edge thereof; a metal cup is shown in solid lines and a plastic cup has its inner openings shown in phantom.

Referring to FIG. 1, a hand-held surgical rotary impact tool 2 is shown having an elongated housing, or body, 4 with a rotatable member 6 at one end and a grip 8 extending downwardly therefrom. An annular extension member 12 is fixed to the front of the elongated housing, or body, 4 around a drive shaft 14 extending from the housing, or body, 4. The annular extension member 12 is fixed to the body 4 by six screws 16 positioned in circular recesses 18 cut into the front surface of the annular extension member 12 and threaded into threaded openings in the front of elongated housing, or body, 4. While Allen screws are shown, other type screws can be used. If desired, the annular extension member 12 can be integral with the housing, or body, 4.

The front end of the drive shaft 14 extends forwardly of the front surface 20 of annular extension member 12 and has diametrical radial slots 21 therein to receive radial extensions, or keys, 22 extending to the side adjacent the end of the drive shaft 14. The rotatable member 6 has a circular recess 24 extending into the center of the rear face 26 thereof to receive the end of the drive shaft 14, and has radial extending grooves 28 opening thereinto to receive the radial extensions, or keys, 22. This construction rotationally fixes drive shaft 14 to the rotatable member 6 so that movement of drive shaft 14 moves rotatable member 6. Threaded openings 30 extend radially inwardly from a cylindrical portion 32 of the exterior of the rotatable member 6, to the outer end of each of the threaded openings 30. A threaded member 34 is located in each threaded opening 30 to be placed against the ends of the radial extensions, or keys, 22 to fix them in position on the end of the drive shaft 14. The rotatable member 6 is axially fixed to the drive shaft by a bolt 25 to be hereinafter described.

Annular extension member 12 has two cylindrical projections 36 projecting forwardly of the front surface 20 for a purpose to be hereinafter described. The rear face 26 of the rotatable member 6 has two arcuate grooves 38 diametrically opposed on each side of drive shaft 14. Cylindrical projections 36, also diametrically opposed, are positioned on the front surface 20 of annular extension member 12 so that each cylindrical projection 36 extends into an arcuate groove 38.

Arcuate grooves 38 are formed having the same arc so that the two cylindrical projections 36 are allowed the same arcuate, or angular, movement therein. This limits the rotational movement of the rotatable member 6. In a surgical tool 2 built, the arc of rotation was 20 degrees. Other desired angles can be used.

The forward part 40 of the rotatable member 6 tapers down to a flat front face 42, from cylindrical portion 32, with a hexagonal recess 44 therein to receive one end 47 of a tool extension 46 having a hexagonal shape 48. The bolt 25, referred to above, has its head located against the bottom of the hexagonal recess 44 and has its threaded rod portion extend through a hole 27 between hexagonal recess 44 and circular recess 24, and it is threaded into a threaded hole in the end of drive shaft 14. The other end 49 of the tool extension 46 has a cylindrical portion 50 with radial extending projections 52. Radial extending projections 52 extend into diametrically opposed notches 102. It is this end 49 of the tool extension 46 which contacts an artificial acetabular cup 100 (see FIG. 5) for removal. Due to the different sizes of people, artificial acetabular, or hip, cups 100 vary in diameter. Therefore, tool extensions having various sized cylindrical portions 50 can provide for various sizes needed. The radially extending projections 52 can be threaded pins which can be radially adjusted to accommodate for a size differential by being mounted in threaded openings 53. Further, plastic cups 100A (see FIG. 5) are made of a thicker wall portion and usually three (3) notches 102A are used. The end 49A of the tool extension 46A is made more spherical in shape, and the radial projections 52A fixed and flat.

The basic rotary impact tool, as mentioned above, can be one of the many pistol grip impact wrenches used to remove wheel lug bolts on cars. The addition of the annular extension member 12 on the front of the housing, or body, 4 around the drive shaft 14, and a rotatable member 6 fixedly connected to the end of the drive shaft 14, along with two fixed forwardly extending projections 36 on the annular extension member 12 which extend into two arcuate grooves 38 of a predetermined length in the rotatable member 6, provides for a desired angular movement of drive shaft 14, with relation to the housing, or body, 4 and therefore, any tool driven thereby.

The drive shaft 14 is driven by a conventional pneumatic drive motor 70 with air directed to the housing, or body, 4 by a hose 60 with the exhaust air being directed away from the housing, or body, 4 by a hose 62. It is noted that an electric motor can be used. An on-off valve 72 is located in housing, or body, 4 in hose 60 to start and stop air flow to the pneumatic drive motor 70. This on-off valve 72 is actuated by a trigger 74 biased to its outer position as shown in FIG. 1, wherein said on-off valve 72 is off and the air flow is stopped. When said trigger 74 is pulled, air under pressure is directed to the pneumatic drive motor 70 to place said rotary impact tool 2 in operation. A repetitive rotary impact force is placed on drive shaft 14 by a conventional hammering unit 80. This action will serve to act to rotate a tool extension 46 to loosen an acetabular cup 100.

Upon loosening of the acetabular cup 100, the cup 100 will only rotate the angular distance permitted by the length of the arcuate grooves 38.

Another control is a reversing valve 76 in the housing, or body, 4 movable between two positions for directing the air under pressure in hose 60 against rotor blades (not shown) in said pneumatic drive motor 70 to drive the drive shaft 14 in (1) a clockwise direction; or (2) a counterclockwise direction. The reversing valve 76 has a push-pull pin 78 extending to the exterior of the housing, or body, 4 for moving the reversing valve between its (1) clockwise and (2) counterclockwise rotating positions.

In a hand-held surgical rotary impact tool 2 built, when the push-pull pin 78 was in its "pushed in" position, the tool would be prepared to rotate in a "clockwise" direction, and when the push-pull pin 78 was in its "pulled out" position, the tool would be prepared to rotate in a "counterclockwise" direction. To properly position the rotatable member 6 before the operation of the surgical tool 2, the rotatable member 6 is rotated by hand to its furthest position in a rotational direction opposite from that the tool 2 is prepared to rotate in.

In the surgical tool built, to prevent an error in positioning, a visual indicating means was used to properly hand position the rotatable member 6 in a "clockwise" position or a "counterclockwise" position, to correspond to the "pulled out" or "pushed in" position, respectively, of the push-pull pin 78. A tag was placed on the back of the surgical tool, above the push-pull pin 78, indicating "pull" with a yellow dot, and "PUSH" with a red dot. Then an indicating line 90, in black, was placed on the annular extension member 12, and two spaced indicating lines C, in red, and CC, in yellow, were placed on the cylindrical portion 32 of the rotatable member 6. These lines, C and CC, were placed apart, indicating the amount of movement of the rotatable member 6 permitted by the arcuate grooves 38 therein and the cylindrical projections 36 of the annular extension member 12. The indicating black line 90 and indicating red line C and yellow line CC, are coordinated so that line C lines up with line 90 when the rotatable member 6 is moved by hand to its furthest counterclockwise position, and line CC lines up with line 90 when the rotatable member 6 is moved by hand to its furthest clockwise position.

Now, when the push-pull pin 78 is "pushed in", the tag indicates that the red line C should be aligned with black line 90; and when the push-pull pin 78 is "pulled out", the tag indicates that the yellow line CC should be aligned with black line 90. If lines are not properly aligned, this is manually done.

While the principles of the invention have now been made clear in an illustrative embodiment, it will become obvious to those skilled in the art that many modifications in arrangement are possible without departing from those principles. The appended claims are, therefore, intended to cover and embrace any such modifications, within the limits of the true spirit and scope of the invention.

I claim:

1. A surgical instrument for removing an artifical acetabular cup comprising a hand-held housing, a motor means therein for rotating both clockwise and counter-clockwise, a drive shaft connected to said motor means extending from said housing, means for rotating said drive shaft both clockwise and counter-clockwise for only a small number of degrees, extension means having one end adapted to be connected to said drive shaft, said extension means having a free end with raidal projections for attachment to an artificial acetabular cup for removal by rotational impact.

2. A surgical instrument as set forth in claim 1 including a fixed housing sleeve on said hand-held housing extending around said drive shaft, said drive shaft having an end projecting through said housing sleeve, and enlarged member fixed to the end of said drive shaft to rotate with it, means interconnecting said housing sleeve and enlarged member to permit only a small degree of rotation of said enlarged member with said housing sleeve, said extension means having one end adapted to be connected to said enlarged member.

3. A surgical instrument as set forth in claim 1 wherein said radial projections are radially adjustable in length to adjust for artificial acetabular cups of different diameters.

4. A surgical instrument as set forth in claim 2 wherein said radial projections are radially adjustable in length to adjust for artificial acetbular cups of different diameters.

5. A surgical instrument as set forth in claim 2 wherein said housing sleeve has a forwardly facing first annular face, said enlarged member having a rearwardly facing second annular face, said second annular face being spaced from said first annular face, one of said annular faces having arcuate groove means therein of a small number of degrees, the other of said annular faces having a fixed projection means extending to said arcuate groove means to limit the rotational movement between the enlarged member and the housing sleeve.

6. A surgical instrument as set forth in claim 1 wherein said radial projections are radially adjustable to provide for different sized artificial acetabular cups.

7. A surgical instrument for removing an artificial acetabular cup comprising, a hand-held housing means, a motor means therein for rotating in a clockwise direction or in a counter-clockwise direction, a drive shaft connected to said motor means, extension means having one end connected to said drive shaft for rotation therewith, said extension means having a free end with radial projections for attachment to an artificial acetabular cup for removal by rotational impact, means for limiting rotation of said drive shaft in a clockwise direction or in a counter-clockwise direction for only a small number of degrees.

8. A combination as set forth in claim 7 wherein said means for limiting rotation includes means interconnecting said drive shaft and said hand-held housing means.

9. A combination as set forth in claim 1 wherein a portion of said hand-held housing means extends around said drive shaft, an enlarged member fixed to said drive shaft to rotate with it, said means for limiting rotation including means interconnecting said enlarged member and said handheld housing means to permit only a small degree of rotation.

10. A surgical instrument as set forth in claim 9 wherein said hand-held housing means has a forwardly facing first annular face, said enlarged member having a rearwardly facing second annular face, said second annular face being spaced from said first annular face, one of said annular faces having arcuate groove means therein of a small number of degrees, the other of said annular faces having a fixed projection means extending into said arcuate groove means to limit the rotational movement between the enlarged member and the housing means.

11. A surgical instrument as set forth in claim 9 wherein said extension means has one end conneted to said enlarged member.

12. A surgical instrument as set forth in claim 7 wherein said radial projections are radially adjustable to provide for different sized artifical acetabular cups.

* * * * *